United States Patent
Hajicek et al.

(10) Patent No.: US 7,754,883 B2
(45) Date of Patent: Jul. 13, 2010

(54) METHOD OF RACEMIZATION OF THE R(−) ISOMER OF THE (2-CHLOROPHENYL)-6,7-DIHYDROTHIENO[3,2-C]PYRIDINE-5(4H)-ACETIC ACID METHYL ESTER

(75) Inventors: Josef Hajicek, Prague (CZ); Hana Stepankova, Cesky Brod (CZ); Jan Kalivoda, Prague (CZ)

(73) Assignee: Zentiva k s, Prague (CZ)

( * ) Notice: Subject to any disclaimer, the term of this patent is extended or adjusted under 35 U.S.C. 154(b) by 219 days.

(21) Appl. No.: 11/885,654

(22) PCT Filed: Mar. 3, 2006

(86) PCT No.: PCT/CZ2006/000010

§ 371 (c)(1),
(2), (4) Date: Sep. 5, 2007

(87) PCT Pub. No.: WO2006/094468

PCT Pub. Date: Sep. 14, 2006

(65) Prior Publication Data

US 2008/0182869 A1    Jul. 31, 2008

(30) Foreign Application Priority Data

Mar. 8, 2005   (CZ) .................... 2005-150

(51) Int. Cl.
  *C07D 495/04*   (2006.01)
(52) U.S. Cl. .................................... 546/114
(58) Field of Classification Search ............. 546/114
  See application file for complete search history.

(56) References Cited

U.S. PATENT DOCUMENTS 6,737,411 B2   5/2004   Valeriano et al.

2004/0024011 A1   2/2004   Valeriano et al.

FOREIGN PATENT DOCUMENTS

| EP | 281459 | 4/1995 |
| EP | 99802 | 2/1997 |
| WO | WO 02/059128 | 8/2002 |

OTHER PUBLICATIONS

International Search Report for International Application No. PCT/CZ2006/000010 mailed Jun. 20, 2006.

*Primary Examiner*—Patricia L Morris
(74) *Attorney, Agent, or Firm*—Pearl Cohen Zedek Latzer, LLP

(57) ABSTRACT

Racemization of the R(−) isomer of the (2-chlorophenyl)-6,7-dihydrothieno[3,2-c]pyridine-5(4H)-acetic acid methyl ester (Formula II) (also called R clopidogrel) is performed via conversion of a portion thereof to the S(+)isomer and it takes place in an organic solvent selected from alcohols, esters, ketones or ethers, or in their mixtures, in the presence of a base selected from substances of formula R1R2R3R4N+OH" wherein R1, R2, R3 and R4 are identical or different substituents selected from C1-C5 alkyls or C5, C6 cycloalkyls or aryls, C7-C9 alkyl-cycloalkyls or alkyl-aryls, the molar ratio of the base to the starting substance being 1:1 to 1:10., OMe Cl I Cl<VOMe II.

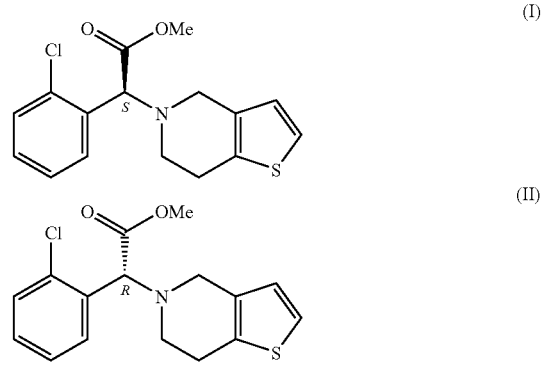

2 Claims, No Drawings

METHOD OF RACEMIZATION OF THE R(−) ISOMER OF THE (2-CHLOROPHENYL)-6,7-DIHYDROTHIENO[3,2-C]PYRIDINE-5(4H)-ACETIC ACID METHYL ESTER

CROSS-REFERENCE TO RELATED APPLICATIONS

This application is a National Phase Application of PCT International Application No. PCT/CZ2006/000010, entitled "METHOD OF RACEMIZATION OF THE R(−) ISOMER OF THE (2-CHLOROPHENYL)-6,7-DIHYDROTHIENO[3,2-C]PYRIDINE-5(4H)-ACETIC ACID METHYL ESTER", International Filing Date Mar. 3, 2006, published on Sep. 14, 2006 as International Publication No. WO 2006/094468, which in turn claims priority from Czechoslovakian Patent Application No. PV 2005-150, filed Mar. 8, 2005, both of which are incorporated herein by reference in their entirety.

TECHNICAL FIELD

The invention concerns a new method of racemization of the R(−) isomer of the (2-chlorophenyl)-6,7-dihydrothieno[3,2-c]pyridine-5(4H)-acetic acid methyl ester, which is the opposite enantiomer of the known antithrombic agent clopidogrel, which is waste during the synthesis.

BACKGROUND ART

The S-(+) isomer of the (2-chlorophenyl)-6,7-dihydrothieno[3,2-c]pyridine-5(4H)-acetic acid methyl ester of formula I

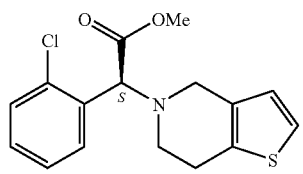

known under the non-proprietary name clopidogrel (or S-clopidogrel), is an effective antithrombic agent, indicated especially for prevention of artherosclerotic events in patients having experienced infarction or stroke or suffering from ischemic disease of lower limbs. It is, therefore, crucial for preventing recurrence of such diseases and, thus, prevents fatal consequences of these diseases.

Process of preparation of clopidogrel (substance of formula I) is described in a number of patents. Those that make up the most relevant part of the prior art with respect to the present invention are cited herein.

In patent EP 99802, a group of substances was described with the antiaggregation effect, which includes also the substance of formula I. In the patent, optically active isomers of these substances are also mentioned. Preparation of substances of the type of clopidogrel (I) was, according to the patent, carried out via reaction of 4,5,6,7-tetrahydro-thieno[3,2-c]pyridine with an alpha-chloro derivative of an alpha-(chlorophenyl)-acetic acid ester in the presence of a base.

Further development published in patent EP 281459 showed that of the substances described in the above mentioned patent hydrogensulfate (the $HSO_4^-$ anion) of substance of formula I is the most advantageous one. This salt was tested for antiaggregation effects and compared with some other salts.

In EP 281459, a method of preparation of this salt is also described, which consists in resolution of the racemic mixture of the substance of formula I with the R isomer of formula II

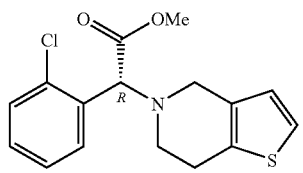

The mixture of substances I and II was transferred to salts of R(−) camphorsulfonic acid in acetone and subsequently crystallized. This was followed with several recrystallizations also from acetone, until sufficiently pure camphorsulfonate of substance I was obtained.

In patent U.S. Pat. No. 6,737,411, an improved method of said resolution is described. It consists in preparation of camphorsulfonic acid in a mixture of C1 up to C12 hydrocarbons with a suitable co-solvent, which is selected from the group including dimethylformamide, butanol or acetone. In a preferable embodiment camphorsulfonic acid is dissolved in dimethylformamide and added to a solution of a mixture of substances I and II in toluene.

Racemization of the undesired enantiomer R, consisting in converting a portion thereof to the S enantiomer and recycling this mixture to the resolving reaction, is described in patent application WO 02/059128, where an inorganic base is used for racemization in the ratio 1:1. While this procedure reliably yields a racemic mixture of the S(+) and R(−) enantiomers, saponification of esters I and II takes place. In order to allow for return of the racemic mixture back to the resolving reaction, it is necessary to convert the alkali salts back to esters. This requires further steps that increase losses and tediousness of the production.

Said drawback has been eliminated by patent U.S. Pat. No. 6,737,411, according to which a catalytic amount of an alcoholate, preferably potassium tert-butanolate, is used. The method leads to a racemic mixture of esters but the reaction can take place only in an absolutely anhydrous environment. That is why the reaction mixture has to be first dried and its water content controlled, which has to be lower than 0.05% (according to KF).

However, we have found a method that leads to a racemic mixture of esters, but that does not require strictly anhydrous environment.

DISCLOSURE OF INVENTION

The invention concerns a method of racemization of the R(−) isomer of (2-chlorophenyl)-6,7-dihydrothieno[3,2-c]pyridine-5(4H)-acetic acid methyl ester (II), (also called R clopidogrel)

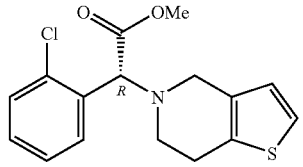

via conversion of a portion thereof to the S(+) isomer of (2-chlorophenyl)-6,7-dihydrothieno[3,2-c]pyridine-5(4H)-acetic acid methyl ester (I) (also called (S)-clopidogrel),

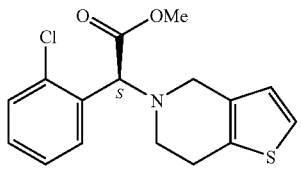

I which takes place in an organic solvent selected from alcohols RaOH, esters of formula Ra(O)ORb, ketones of formula Ra(O)Rb or ethers of formula RaORb, or in a mixture thereof, wherein Ra and Rb independently represent an aliphatic C1-C5 substituent or an aromatic C5-C8 substituent, in the presence of base selected from substances of formula $R^1R^2R^3R^4N^+OH^-$ wherein $R^1$, $R^2$, $R^3$ and $R^4$ are identical or different substituents selected from C1-C5 alkyls or C5, C6 cycloalkyls or aryls, C7-C9 alkyl-cycloalkyls or alkyl-aryls, the molar ratio of the base to the starting substance being 1:1 to 1:10.

The method is based on surprisingly advantageous properties of alkyl-, aryl- or cycloalkyl-ammonium hydroxides, which catalyze racemization already in low molar ratios to the reacting substance (1:10), however, ratios 1:2 to 1:4 have turned up to be more advantageous. However, these substances do not cause saponification of esters even in an equimolar combination.

Of the series of ammonium hydroxides that are useful in the reaction, the commercially available ones, or the cheapest compounds will be preferably selected. In a preferred embodiment, therefore, substituents $R^1$, $R^2$, $R^3$ and $R^4$ represent a C1-C5 alkyl, more preferably $R^1=R^2=R^3=R^4$ and represent methyl or butyl.

The choice of solvents is associated with solubility of the two agents. Accordingly, the reaction can be carried out in alcohols of formula RaOH, wherein Ra is an aliphatic C1-C5 substituent or an aromatic C5-C8 substituent, in esters of formula Ra(O)ORb, wherein Rb is also an aliphatic C1-C5 substituent or an aromatic C5-C8 substituent, or in ketones of formula Ra(O)Rb, or ethers of formula RaORb or in a mixture of such solvents.

Considering the wide range of the solvents that can be chosen for racemization according to the invention, it is possible to make such a choice that racemization occurs in the same solvent in which resolution of substances I and II and separation of the undesired (S)-isomer have occurred. The mother liquors, in which the (R)-isomer II predominates, are subjected to racemization without further isolation and eventually, a mixture of the R and S isomers of clopidogrel, i.e. of substances I and II, is isolated.

With respect to successfulness of separation of the undesired S isomer I, dissolving the starting mixture of I and II in an ester of formula Ra(O)ORb, preferably isopropyl acetate, followed by reacting with a solution of R-camphorsulfonic acid in a solvent of formula RaOH, preferably methanol, appears to be a very suitable combination. After separating the salt of S-clopidogrel by crystallization, a hydroxide $R^1R^2R^3R^4N^+OH$ (wherein the symbols are as defined above) is added to the mother liquors (meaning of symbols is described above), preferably commercially available hydroxides wherein $R^1$, $R^2$, $R^3$ and $R^4$ are aliphatic substituents, such as tetramethylammonium hydroxide or tetrabutylammonium hydroxide, in a solution of RaOH, preferably in methanol.

Such procedure allows for economical design both for preparation of S-clopidogrel I, suitable for medical use, and for racemization according to the invention.

The reaction mixture is initially cooled down to 0 to 10° C. and after 1 to 5 hours, the reaction can finish at normal temperature, i.e. about 20 to 25° C. Usual reaction time is 10 to 24 hours.

EXAMPLES

The invention is further illustrated using the following examples.

Abbreviations used in examples have following meanings:

(TMAH) tetramethylammonium hydroxide (TBAH) tetrabutylammonium hydroxide

Example 1

2.53 g of (R)-clopidogrel (7.86 mmol) was dissolved in 50 ml of methanol. The resulting solution was cooled down in a water+ice bath to a temperature of +5 to +10° C. and 1.65 ml (3.93 mmol) of a 25% solution of TMAH in methanol was added to the solution. The resulting solution was stirred in the cooling bath at temperatures +5 to +10° C. for 2.5 hours. The cooling bath was then removed and the solution was let to temper to room temperature. At this temperature, the reaction mixture was stirred for another 20 hours. After this time, methanol was evaporated from the solution in a rotatory vacuum evaporator and the evaporation residue was divided between 20 ml of water and 20 ml of dichloromethane. The dichloromethane layer was dried with anhydrous magnesium sulfate and evaporated in a rotatory vacuum evaporator.

1.75 g (69.2%) of a racemic mixture of R clopidogrel and S clopidogrel was obtained.

$[\alpha]_D=-0.5°$; MeOH.

Analysis using capillary electrophoresis demonstrated presence of (R)-clopidogrel:(S)-clopidogrel in the ratio 50:50.

$^1$H NMR spectra (250 MHz, CDCl$_3$): δ 7.71 m (1H), 7.40 m (1H), 7.23-7.31 m (2H), 7.07 d (5 Hz) (1H), 6.76 d (5.0 Hz) (1H), 4.94 s (1H), 3.81 m (2H), 3.72 s (3H), 2.88 m (2H), 2.74 m (2H).

$^{13}$C NMR spectra (62.9 MHz, CDCl$_3$): δ 171.3, 134.7, 133.8, 133.5, 132.4, 130.0, 129.8, 129.4, 127.2, 126.9, 122.4, 67.5, 52.1, 49.7, 48.0, 25.6.

Example 2

9.48 g of (R)-clopidogrel (29.45 mmol) was dissolved in 75 ml of i-propylacetate. The resulting solution was cooled down in a water+ice bath to a temperature of +5 to +10° C. and 6.2 ml (14.72 mmol) of a 25% solution of TMAH in methanol was added to the solution. The resulting solution was stirred in the cooling bath at temperatures +5 to +10° C. for 4 hours. The cooling bath was then removed and the solution was let to temper to room temperature. At this temperature, the reaction mixture was stirred overnight. 10 ml of water was then added to the reaction mixture. Water was separated and the organic phase was extracted once more with 20 ml of water, dried with anhydrous magnesium sulfate and evaporated in a rotatory vacuum evaporator.

6.9 g (72.9%) of racemic clopidogrel was obtained.

$[\alpha]_D=0°$; MeOH.

Example 3

A solution of 35.8 g (R)-clopidogrel (0.111 mol) in 350 ml of i-propylacetate was cooled down in a water+ice bath to a temperature of +5 to +10° C. and 42.5 ml (55.62 mmol) of a 40% solution of TBAH in methanol was added to the solution. The resulting solution was stirred in the cooling bath at temperatures +5 to +10° C. for 2 hours. The cooling bath was then removed and the solution was let to temper to room temperature. At this temperature, the reaction mixture was stirred for 17 hours. The reaction mixture was then extracted with 2×150 ml of water, dried with anhydrous magnesium sulfate and evaporated in a rotatory vacuum evaporator.

35.4 g of racemic clopidogrel was obtained.

$[\alpha]_D = -0.5°$; MeOH.

Example 4

A solution of 73.57 g of (R)-clopidogrel (0.2286 mol) in 900 ml of i-propylacetate was cooled down in a water+ice bath to temperatures +5 to +10° C. and 48.18 (55.62 mmol) of a 25% solution of TMAH in methanol was added to the solution over 15 minutes. The resulting solution was stirred in the cooling bath at temperatures +1 to +2° C. for 2.5 hours. The cooling bath was then removed and the solution was let to temper to room temperature. At this temperature, the reaction mixture was stirred overnight. The reaction mixture was then extracted with 2×150 ml of water, dried with anhydrous magnesium sulfate and evaporated in a rotatory vacuum evaporator.

73.0 g of a racemic mixture of R clopidogrel and S clopidogrel was obtained.

$[\alpha]_D = -1.0°$; MeOH.

Example 5

An i-propylacetate solution of the base (3.134 kg of a mixture of R clopidogrel and S clopidogrel (1:1); 4.96 mol in 14 liters of i-propylacetate) is charged into a boiler fitted with a thermometer, a cooler and a calcium-chloride tube. While stirred, the solution is heated in a water bath to a temperature 45 to 50° C. A pre-prepared solution of (R)-(−)-10-camphorsulfonic acid in methanol (1.160 kg of the acid in 1200 ml of methanol) was added to the warm solution. Then, 12 l of i-isopropylacetate was added to the clear solution at a temperature 45 to 50° C.

Cooling down the solution to temperature of about 20 to 25° C. is started. The solution is inoculated and let to crystallize under stirring first at temperature 20-25° C. for 2 hours. Then, cooling down the solution to temperature 5 to 10° C. is started and the solution is crystallized at this temperature for 3 hours.

The resulting crystals are sucked off through a Büchner funnel and washed with a minimal amount of i-propylacetate (about 0.5 l). 1560 g of (S)-clopidogrel camphorsulfonate was obtained. The mother liquors after crystallization are processed by the procedure described in Example 6.

Example 6

1 l of i-propylacetate mother liquors from Example 5 was extracted with 2×150 ml of a 10% NaHCO$_3$ solution. The organic layer was separated and dried with anhydrous MgSO$_4$. The desiccant was removed by filtration and 500 ml of an i-propylacetate solution, which contained 45.73 g (0.142 mol) of the clopidogrel base, was charged into a three-neck flask fitted with a thermometer, a magnetic stirrer and a dropping funnel. The i-propylacetate solution was cooled in a water+ice bath to the temperature +2° C. Then, a solution of TMAH (26 g of a 25% methanolic solution) was added drop by drop over 10 minutes. The reaction mixture was cooled to the temperature +2° C. for 2.5 hours. It was then slowly tempered to room temperature and stirred at this temperature for 19 hours. The reaction mixture was then extracted with 2×80 ml of distilled water. The i-propylacetate solution of the base was evaporated and 44.08 g of a mixture of the R clopidogrel base and the S clopidogrel base was obtained; $[\alpha]_D = 0°$; MeOH.

Example 7

The mixture of the R and S clopidogrel bases from the previous Example was dissolved in 144 ml of i-propylacetate and a solution of 16.21 g of (R)-(−)-10-camphorsulfonic acid in 16.8 ml of methanol was added to this solution at the temperature 50° C. Another 168 ml of i-propylacetate was added to the resulting solution. The reaction mixture was then cooled down to room temperature and stirred at this temperature for 2 hours. Then, the reaction mixture was crystallized at +5° C. for 48 hours. It was then sucked off and washed with a small amount of i-propylacetate. 20.5 g of (S)-clopidogrel camphorsulfonate was obtained.

The invention claimed is:

1. A method of preparation of the S(+) isomer of the (2-chlorophenyl)-6,7-dihydro-thieno[3,2-c]pyridine-5(4H)-acetic acid methyl ester of formula I

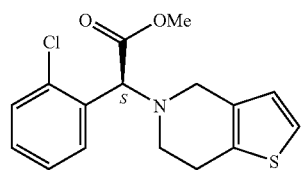

wherein a mixture of R and S isomers of clopidogrel is dissolved in an ester of formula Ra(O)ORb, wherein Ra and Rb independently represent a C1-C5 aliphatic substituent or a C5-C8 aromatic substituent, and a solution of R-camphorsulfonic acid in a solvent of formula RaOH is added to the solution, from the mixed solution the camphorsulfonic salt of the substance of formula I is crystallized, which is converted to S(+) isomer of the (2-chlorophenyl)-6,7-dihydro-thieno[3,2-c]pyridine-5(4H)-acetic acid methyl ester of formula I in the next step; further a base of formula $R^1R^2R^3R^4N^+OH^-$ wherein $R^1$, $R^2$, $R^3$ and $R^4$ are identical or different substituents selected from C1-C5 alkyls or C5, C6 cycloalkyls or aryls, C7-C9 alkyl-cycloalkyls or alkyl-aryls in a solution in a substance of formula RaOH is added to the mother liquors after crystallization, thus resulting in a mixture of R and S isomers of clopidogrel, that are used for preparation of S(+) isomer of the (2-chlorophenyl)-6,7-dihydro-thieno[3,2-c]pyridine-5(4H)-acetic acid methyl ester of formula I.

2. The method according to claim 1 wherein the substance of formula RaOH is methanol and the ester of formula Ra(O)ORb is isopropylacetate.

* * * * *